US005391150A

United States Patent [19]
Richmond

[11] Patent Number: 5,391,150
[45] Date of Patent: Feb. 21, 1995

[54] IV BAG WITH NEEDLELESS CONNECTOR PORTS

[76] Inventor: Frank Richmond, 205 A Grant St., Harvard, Ill. 60033

[21] Appl. No.: 997,610

[22] Filed: Dec. 28, 1992

[51] Int. Cl.6 ...................... A61M 5/00; A61M 37/00; A61B 19/00

[52] U.S. Cl. ...................................... 604/111; 604/91; 604/247; 604/408

[58] Field of Search .................. 137/493.9, 512.4, 843, 137/846, 847, 848, 849, 850, 852, 854, 855; 222/92, 96, 94, 95, 490, 491, 494; 251/149.1, 149.7; 604/9, 30, 31, 80, 91, 83, 81, 86, 246, 247, 257, 262, 408, 410, 415, 185, 111

[56] References Cited

U.S. PATENT DOCUMENTS

| | | | |
|---|---|---|---|
| 4,354,492 | 10/1982 | McPhee | 604/81 |
| 4,556,086 | 12/1985 | Raines | 137/843 |
| 4,683,916 | 8/1987 | Raines | 604/247 |
| 4,838,875 | 6/1989 | Somor | 604/262 |
| 4,852,560 | 8/1989 | Hermann, Jr. et al. | 128/762 |
| 4,908,018 | 3/1990 | Thomsen | 604/247 |
| 4,946,448 | 8/1990 | Richmond | 137/843 |
| 5,116,021 | 5/1992 | Faust et al. | 251/149.1 |
| 5,190,067 | 3/1993 | Paradis et al. | 251/149.1 |

*Primary Examiner*—John D. Yasko
*Assistant Examiner*—Adam J. Cermak
*Attorney, Agent, or Firm*—John L. Rogitz

[57] ABSTRACT

An IV bag has at least one opening and a valve associated with the opening. The valve is normally closed to prevent fluid communication through the opening. A needleless connector can be engaged with the valve to open the valve and thereby establish a passageway for fluid communication through the opening.

1 Claim, 3 Drawing Sheets

IV BAG WITH NEEDLELESS CONNECTOR PORTS

FIELD OF THE INVENTION

The present invention relates generally to intravenous (IV) infusion equipment, and more particularly to IV bags and IV sets.

BACKGROUND OF THE INVENTION

One of the most widely used methods of medical therapy is the intravenous (IV) infusion of medicaments and/or nutrients into the bloodstream of a patient. A familiar apparatus that is used in many IV infusion applications is the IV bag. The IV bag contains the fluid to be infused into the patient. Typically, one end of an IV line is attached to the IV bag in communication with the fluid in the IV bag, and the other end of the IV line is connected to a needle that can puncture the patient to thereby establish a path for fluid communication from the IV bag to the patient. Usually, the bag is elevated above the patient to establish a positive pressure head to force the fluid that is within the bag into the patient.

Accordingly, an IV bag must have at least one opening through which fluid can flow. Many IV bags, however, have more than a single opening, to establish both a pathway for extracting fluid from the bag and a pathway for injecting fluid into the bag. Specifically, many bags have one or more openings in the bottom seam of the bag, and tubes are respectively connected to the openings. Each tube has a membrane disposed therein. In one application, the membrane can be pierced by inserting a so-called IV spike into the tube. The spike is usually connected to a drip chamber and the drip chamber in turn is connected to the IV line to the patient. The spike must ordinarily remain connected to the tube until the contents of the bag have been exhausted because the membrane is not resealable when the spike is extracted from the tube.

In another application, a resealable membrane is provided in the tube, and the resealable membrane can be punctured by the needle of a syringe to inject additional fluid from the syringe into the bag. After fluid injection, the needle can be withdrawn, and the membrane reseals to prevent fluid flow through the opening.

In addition to the openings in its bottom seam, an IV bag can have an opening in its sides or top seam. A pierceable resealable membrane can be positioned in each of the openings, and the needle of a syringe can be advanced through the membrane. Fluid in the syringe can then be injected into or extracted from the bag through the needle. After fluid injection or extraction, the needle can be withdrawn from the bag, at which time the membrane reseals. When such an arrangement is on the side of the container, the arrangement is colloquially known as a "belly button."

Unfortunately, each of the arrangements mentioned above has certain drawbacks. For example, the arrangements that are used with syringes require the use of a sharpened needle or spike to pierce the respective membranes. The use of sharpened needles and spikes, however, raises the possibility that a health care worker could inadvertently puncture the bag or himself with the needle or spike. Besides being uncomfortable for the health care worker, the specter of transmitting infectious diseases via the needle or spike is raised by such mishaps, which can have tragic consequences, particularly in the era of AIDS. Thus, the use of needles and other "sharps" should be avoided whenever possible in the health care environment.

While a spike is ordinarily not considered to be a "sharp," the existing membrane arrangements requiring the use of a spike do not permit removal of the spike from the bag Until the contents of the bag are completely exhausted. This is because the hole a spike makes in a membrane is typically too large to permit the membrane to reseal. Thus, once inserted, a spike is not usually removed from an IV bag until the bag is empty, which can understandably limit use of the bag.

Accordingly, it is an object of the present invention to provide an IV bag which does not require the use of "sharps" to infuse or extract fluid from the bag and which has tamper-resistant connector ports. Another object of the present invention is to provide an IV bag that permits the removal of a set from the bag before the bag is empty, with the option of recapping the bag. Yet another object of the present invention is to provide an IV bag that is easy to use and cost-effective to manufacture.

SUMMARY OF THE INVENTION

An intravenous (IV) container, preferably an IV bag, has at least one opening, and the opening has an associated valve which selectively blocks fluid flow through the opening. In accordance with the present invention, the valve is normally shut (i.e., the valve is biased into a shut configuration), and a needleless connector can be engaged with the valve to open the valve. A passageway for fluid flow is thereby established through the valve, through which fluid can be infused into or extracted from the bag.

In one presently preferred embodiment, the needleless connector can be a male luer fitting. One end of the luer fitting is connected to an IV line, and the other end of the luer fitting is engaged with the valve. Alternatively, one end of the luer fitting can be attached to a needleless syringe, and the other end of the luer fitting is engaged with the valve. In either of these embodiments, the valve is disposed in an opening that is formed through the side of the IV bag.

In another embodiment, a tube is connected to an opening that is formed in the bottom, sides or top seam of the IV bag, and the valve is disposed in or on the tube. The valve can be opened by engaging it with a suitable needleless connector, such as a needleless IV spike. In yet a third embodiment, a single IV bag can have a plurality of one or both of the openings and valves described above.

In another embodiment, noncompatible fluids or powder/diluent (i.e., drugs) can be mixed or transferred from one chamber of a multi-compartmental container to another.

In accordance with the present invention, the valve includes a hollow body defining a fluid passageway, and a valve seat circumscribes the fluid passageway. Additionally, the valve includes a resilient valve disc that is positioned in the fluid passageway and is biased into a closed position, wherein the disc abuts the valve seat and thereby blocks fluid flow through the fluid passageway. The disc is movable to an open position, wherein the disc is distanced from the valve seat so that fluid flow is permitted through the fluid passageway.

As contemplated by the present invention, the valve body has a support element which is positioned on the valve body between the valve disc and the inside of the IV bag for supporting the valve disc at the center of the disc. Also, the valve body includes a retainer element that is positioned on the opposite side of the disc from the support element, to hold the center of the disc against the support element.

In the presently preferred embodiment, the valve has an urging member that is reciprocally disposed in the fluid passageway of the valve on the same side of the disc as the retainer element. This urging member is movable between a first position, wherein the urging member is distanced from the valve disc, and a second position, wherein the urging member contacts the valve disc to move the disc into its open position. The urging member is moved to its second position by advancing a needleless connector into the fluid passageway against the urging member.

These and other aspects of the present invention can best be appreciated in reference to the accompanying drawings in which like numerals refer to like parts, and in which:

BRIEF DESCRIPTION OF THE DRAWINGS

FIG. 5 is a perspective view of an alternate embodiment.

DESCRIPTION OF THE PREFERRED EMBODIMENT

Figure 1:
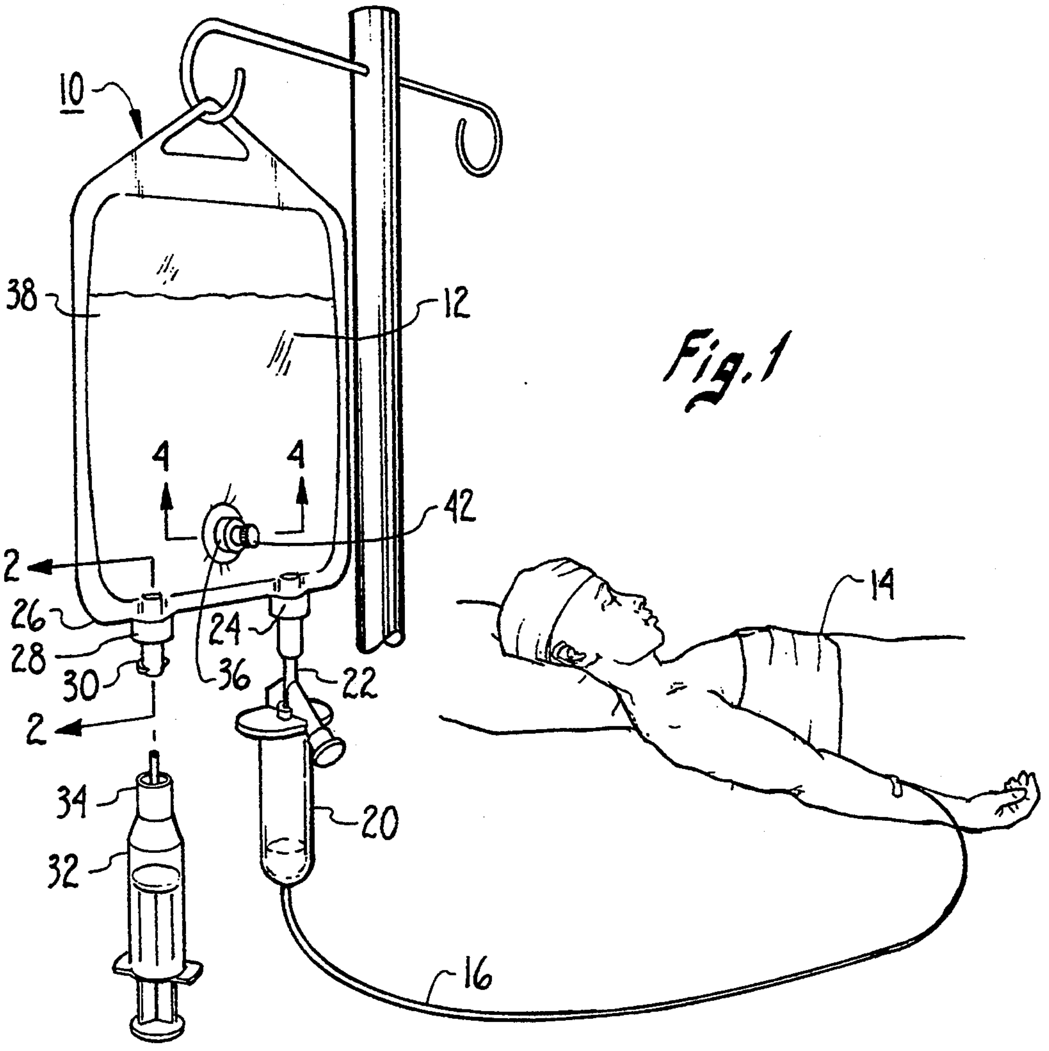
FIG. 1 is a perspective view of the IV bag of the present invention, shown in one intended environment.
Figure 1A:
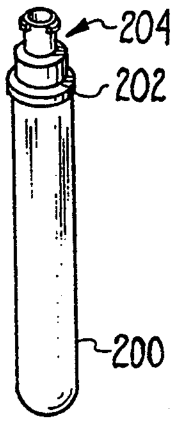

Referring initially to FIG. 1, an intravenous (IV) infusion bag is shown, generally designated 10. Preferably the bag 10 is made of a suitable inert, biocompatible, flexible material, such as polyvinylchloride (PVC) or plex dr. It is to be understood, however, that the principles of the present invention can be applied to other types of IV fluid containers, such as semi-rigid containers (not shown), or glass bottles and vials (FIG. 5).

As shown in FIG. 1, the bag 10 holds a fluid 12 to be infused into a patient 14 through IV line 16. It is to be understood that the IV line 16 may be operably engaged with respective devices, such as roller clamps (not shown) for selectively permitting fluid communication through the IV line 16.

FIG. 1 shows that the IV line 16 is connected to a conventional drip chamber 20, and the drip chamber 20 is in turn connected to a conventional spike 22. The spike 22 is engaged with a conventional port 24 of the bag 10. As shown in FIG. 1, the port 24 is essentially a tube that has a first end inserted into an opening in the IV bag 10 at the bottom seam 26 of the IV bag 10. The conventional port 24 has a membrane (not shown) positioned therein, and the spike 22 pierces the membrane to establish a path for fluid communication between the spike and the interior of the IV bag.

Still referring to FIG. 1, the bag 10 also has a needleless port 28 that includes a tube which is inserted into an opening in the bottom seam 26 of the bag 10 and then bonded by means well-known in the art (e.g., ultrasonic welding, solvent bonding, heat staking, spin welding or rf sealing). Alternatively, the tube of the port 28 can be formed integrally with the IV bag 10, or the tube can be bonded internally to the bag 10.

FIG. 1 further shows that the port 28 includes a valve 30. A needleless syringe 32 can be operably engaged with the needleless port 28. Preferably, for purposes to be disclosed below, the needleless syringe 32 has an end 34 configured as a male luer fitting, to facilitate engagement of the syringe 32 with the needleless port 28. The syringe 32 can be used to inject additional fluid into the bag 10. Alternatively, a needleless spike (not shown) having an end configured as a male luer fitting can be engaged with the needleless port 28 to establish a passageway for fluid infusion from the bag 10 into an IV line (not shown) and thence into the patient 14.

While FIG. 1 shows a needleless port 28 and a conventional port 24, it is to be understood that additional needleless ports (not shown) can be included in the bag 10. It is to be further understood that the conventional port 24 can be omitted from the bag 10, or additional conventional ports (not shown) included in the bag 10. In any case, the ports 24, 28 that extend from the bottom seam 26 of the bag 10 can be formed integrally with the bag 10 or attached to the bag 10 by well-known means, e.g., by rf sealing, ultrasonic welding, heat staking, spin welding, or solvent bonding.

In addition to the ports 24, 28 that extend from the bottom seam 26 of the bag 10, FIG. 1 shows that another port 36, colloquially known as a "belly button," can be formed in a side surface 38 of the bag 10. Preferably, the belly button port 36 includes an opening in the side surface 38 of the bag 10, and a valve 42 is disposed in the opening. A needleless syringe (not shown), e.g., a syringe having a male luer fitting in lieu of a sharp needle, can be engaged with the belly button port 36 to inject or extract fluid from the bag 10.

Figure 2A:
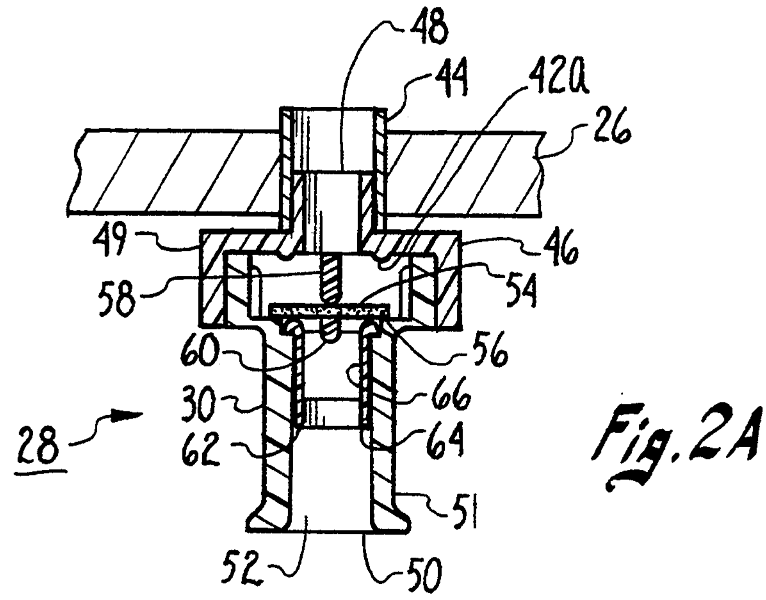
FIG. 2A is a cross-sectional view of one of the valves of the IV bag, as seen along the line 2—2 in FIG. 1, with the valve in the closed position.

Now referring to FIG. 2A, the details of the needleless port 28 can be seen. As shown, the needleless port 28 includes a hollow tube 44, and the valve 30 is positioned in the tube 44 to selectively prevent fluid communication through the tube 44. The valve 30 includes a rigid, preferably plastic (e.g., PVC) valve body 46 that has a fluid inlet 48, a fluid outlet 50, and a fluid passageway 52 formed in the valve body 46 between the inlet 48 and outlet 50. The valve body 46 can be a unitary structure, or be made of two or more pieces that are bonded together, as shown. For example, the inlet 48 can be formed from a first piece 49, the outlet 50 can be formed from a second piece 51, and the two pieces can be bonded together by means well-known in the art, e.g., solvent bonding, ultrasonic sealing, or rf welding.

Figure 3:
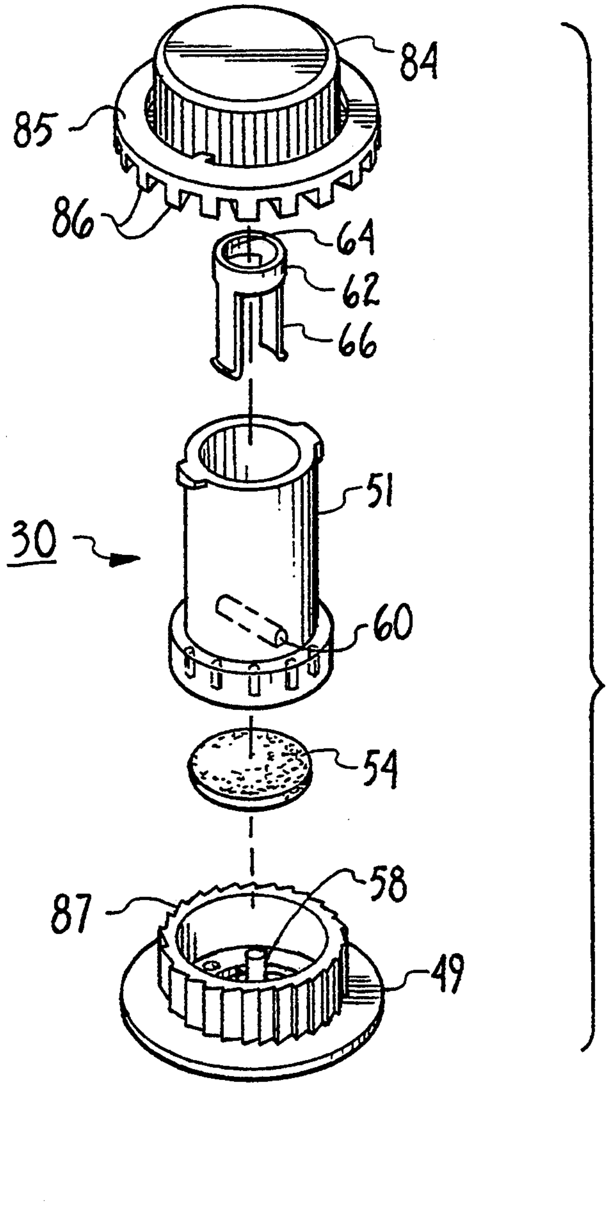
FIG. 3 is an exploded view of the valve shown in FIG. 2A, with portions of the tamper-proof cap broken away, or shown in phantom for clarity.

In cross-reference to FIGS. 2A and 3, the valve 30 also includes a flexible resilient plastic or silicon rubber disc 54 that is disposed in the fluid passageway 52. Specifically, the periphery of the plastic disc 54 rests on a seating surface 56 of the valve body 46 to establish a fluid-tight seal between the disc 54 and seating surface 46. In other words, the valve disc 54 is biased to the closed configuration shown in FIG. 2A. A support element 58 is formed in the fluid passageway 52 and extends across the fluid passageway 52.

The support element 58 supports the disc 54 in the center thereof. To this end, a slight depression may be formed in the center of the disc 54 to receive the support element 58 and thereby prevent side-to-side motion of the disc 54 relative to the support element 58. As shown, the support element 58 is shaped as a cylinder, but it is to be understood that the support element 58 can have other suitable shapes, e.g., the support element 58 can have a triangular shape.

Additionally, a retainer element 60 is formed on the valve body 46 and extends across the fluid passageway 52. As shown, the retainer element 60 is positioned on the valve body 46 on the opposite side of the valve disc 54 from the support element 58. Accordingly, the retainer element 60 holds the center of the valve disc 54 against the support element 58.

Still referring to FIGS. 2A and 3, a rigid urging member 62 is shown slidably disposed in the fluid passageway 52 for reciprocal movement therein. As shown, the urging member 62 has an annular head 64 and a skirt 66 that depends from the head 64. As further shown, the skirt 66 includes a plurality of, preferably two, legs. The urging member 62 can be forced against the valve disc 54 by advancing an appropriate connector fitting (not shown), such as a male luer fitting, into the fluid passageway 52 and against the urging member 62.

Figure 2B:
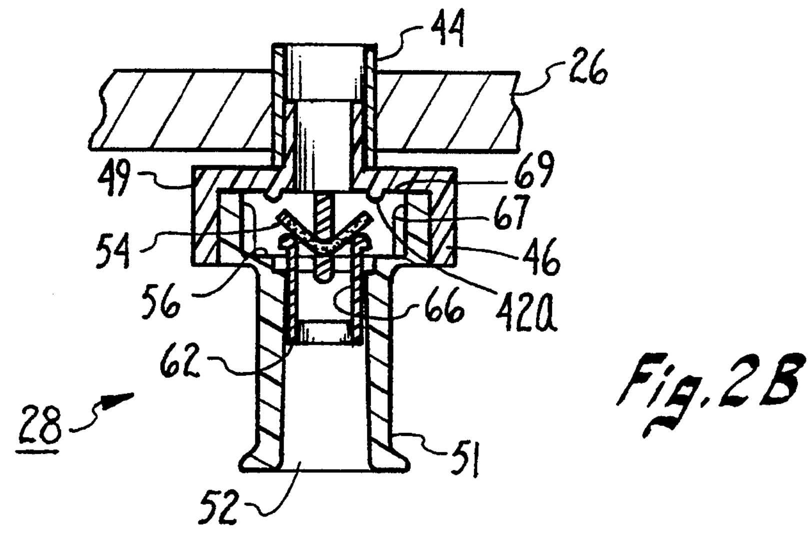
FIG. 2B is a cross-sectional view of one of the valves of the IV bag, as would be seen along the line 2—2 in FIG. 1, with the valve in the open position.

As shown in FIG. 2B, when the urging member 62 is forced against the valve disc 54, the skirt 66 of the urging member 62 contacts the surface of the disc 54. This deforms the valve disc 54, causing the sealing surface of the disc 54 to be distanced from the seating surface 56 of the valve body 46, and thereby permitting fluid communication through the fluid passageway 52. Stated differently, a needleless connector can be advanced into the fluid passageway 52 to force the urging member 62 against the valve disc 54 and deform the disc 54 into an open configuration. When the needleless connector is retracted from the fluid passageway 52, the resiliency of the valve disc 54 causes the disc 54 to resume its normally closed configuration, shown in FIG. 2A.

Referring back to FIG. 3, a tamper-resistant cap 84 can be engaged with the valve 30. In one presently preferred embodiment, a skirt 85 of the cap brim 84 has a plurality of resilient ratchet threads 86. The ratchet threads 86 are configured generally as right triangles, as shown, and permit rotation of the cap 84 in the clockwise direction relative to the valve 30 to thereby engage the cap 84 with the valve 30. The threads 86 do not, however, permit easy rotation of the cap 84 in the counter clockwise direction. The threads 86 ratchetably engage blades 87 that are formed on the first piece 49. It is to be understood that the cap 84 can engage any appropriate surface of the first piece 49.

Figure 4A:
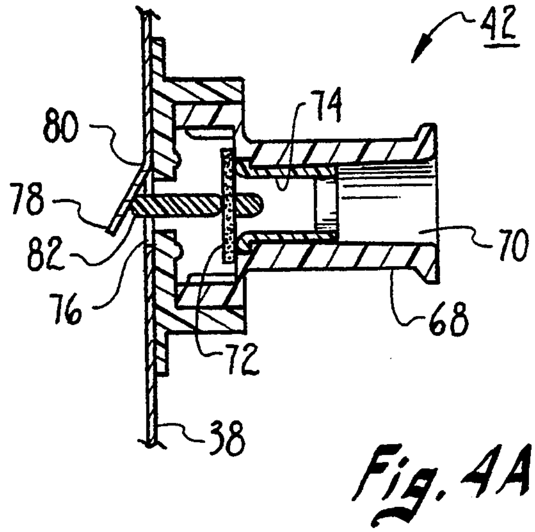
FIG. 4A is a cross-sectional view of another one of the valves of the IV bag, as seen along the line 2—2 in FIG. 1, with the valve in the closed position.
Figure 4B:
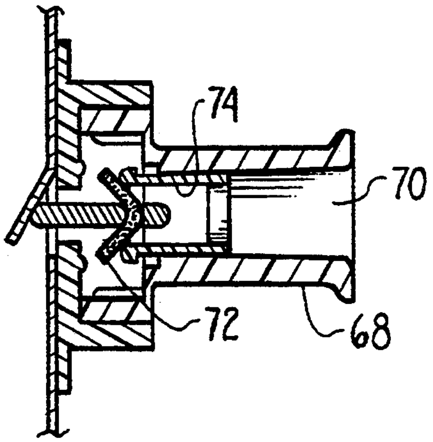
FIG. 4B is a cross-sectional view as would seen along the line 2—2 in FIG. 1, with the valve in the open position.

FIGS. 4A and 4B show that the valve 42 is, in all essential respects, identical to the valve 30. Specifically, the valve 42 has a valve body 68 forming a fluid passageway 70. A valve disc 72 is positioned in the fluid passageway 70 for selectively blocking fluid communication therethrough. An urging member 74 is disposed in the fluid passageway 70 for reciprocal movement therein, and a needleless connector (not shown) can be advanced into the fluid passageway 70 against the urging member 74 to open the valve 42.

The valve 42 is attached, as by solvent bonding, spin welding, rf welding, or ultrasonic sealing, to the side 38 of the bag 10. An opening 76 is formed in the side 38 of the bag 10, for establishing a pathway for fluid communication into and out of the bag 10. The opening 76 can be formed in the side 38 of the bag 10 during manufacture of the bag 10 by cutting out a portion of the bag 10. More preferably, a die cut is made in the side 38 of the bag 10 in a partially circular pattern to form a flap 78. The flap 78 remains attached to the bag 10 by an uncut nick 80, and a protrusion 82 is formed on the valve 42 for urging against the flap 78 to unblock the opening 76 when the valve 42 is attached to the bag 10. Thereby, the flap 78 does not prevent fluid flow through the opening 76, once the valve 42 is in place, and the flap 78 does not become detached from the bag 10. This ensures that the flap 78 will not enter the fluid in the bag 10 and thus will not foul any of the IV components discussed above. Alternatively, the flap 78 can be separated from the bag 10 during manufacturing, and the protrusion 82 omitted from the valve 42.

Specifically, to disengage the cap 84 from the valve 30, sufficient torque must be imparted to the cap 84 to strip to ratchet threads 86. Consequently, once the cap 84 has been removed from the valve 30, it cannot be re-engaged with the valve 30. Thus, a missing or stripped cap 84 indicates that the cap 84 has been tampered with. It is to be understood that if desired, a new cap (not shown) that is in all essential respects identical to the cap 84 can be engaged with the valve 30.

In the operation of the bag 10, reference is made to FIG. 1. With the bag 10 initially full of fluid to be infused into the patient 14, the valves 30, 42 are closed to prevent fluid flow through the ports 28, 36. In other words, the valve discs 54, 72 are biased into their normally closed configurations. Also, the membrane within the conventional port 24 prevents fluid flow through the conventional port 24.

A path for fluid communication can be established through any one of the ports 24, 28, 36 by advancing an appropriate connector into the particular port, For example, fluid 12 from the bag 10 can be infused into the patient 14 by advancing a needleless spike (not shown) into the needleless port 28. Alternatively, fluid can be added to or extracted from the bag 10 by advancing the end 34 of the needleless syringe 32 into the port 28 and operating the plunger of the syringe 32 to inject fluid into the bag 10.

More particularly, as described above, the needleless syringe 32 is sufficiently advanced into the needleless port 28 (and the valve 30) to open the valve 30. Fluid 12 can then be injected into or extracted from the IV bag 10 through the needleless port 28.

Similarly, the conventional spike 22 can be advanced into the conventional port 24 until the spike 22 pierces the membrane within the port 24. This establishes a path for fluid flow through the port 24, spike 22 and IV line 16 into the patient 14. This fluid flow can be effected by gravity drain or by engaging a peristaltic pump (not shown) with the IV line 18 and pumping fluid 12 into the patient 14.

Further, fluid can be injected or extracted from the IV bag 10 by engaging a needleless syringe with the belly button port 36 and appropriately operating the plunger of the syringe. More specifically, using the belly button port 36 as an example, the connector portion of the syringe can be advanced into the valve 42 to open the valve 42, and the plunger of the syringe then manipulated as appropriate to infuse or extract fluid into the bag 10.

When it is no longer necessary to infuse fluid into the bag 10 through the needleless port 28, the needleless syringe 32 is simply retracted from the needleless port 28. This causes the resilient valve disc 54 to resume its normally closed position to thereby block fluid flow through the needleless port 28. Also, after fluid has been infused or extracted as appropriate from the bag 10 through the belly button port 36, the needleless syringe is simply retracted from the valve 42. This causes the resilient disc 72 to resume its normally closed configuration, thereby preventing fluid flow through the bellow button port 36. FIG. 5 shows that a glass vial 200 can have a needleless port 202. A valve 204 which is in all essential respects identical to the valve 30 can be positioned in the port 202, to selectively establish a needleless connector through which fluid can pass into or out of the vial 200.

While the particular IV bag as herein shown and described in detail is fully capable of attaining the objects stated above, it is to be understood that it is but the presently preferred embodiments of the present invention, and that the scope of the present invention is accordingly to be limited by nothing other than the appended claims.

I claim:

1. A device for holding fluid to be infused to a patient, comprising:

a hollow container having flaccid walls for holding the fluid, the container having an opening formed therein;

a valve positioned within the opening to selectively block fluid communication therethrough, the valve being operable by engagement with a spikeless or needleless IV component, the valve including:

a hollow body defining a fluid passageway therethrough, the body being formed with a luer fitting and a plurality of ratchet teeth;

a resilient valve disc positioned in the fluid passageway and being biased into a closed configuration, wherein the disc blocks fluid flow through the fluid passageway, the disc being movable to an open configuration wherein fluid flow is permitted through the fluid passageway;

a support element positioned on the valve body between the valve disc and the inside of the container for supporting the valve disc at the center of the disc;

at least one protrusion found on the body for contacting the disc in the open configuration:

a retainer element positioned in the valve on the opposite side of the disc from the support element, to hold the center of the disc against the support element;

an urging member reciprocally disposed in the fluid passageway of the valve on the same side of the disc as the retainer element, the urging member being movable between a first position, wherein the urging member is distanced from the valve disc, and a second position, wherein the urging member is contacted by a syringe to cause the urging member to contact the valve disc to move the disc into its open configuration; and a cap including a plurality of blades for engaging the ratchet teeth to cover the luer fitting and to permit rotation of the cap relative to the valve body in a first direction, and to cause the blades to strip when the cap is rotated in a direction opposite to the first direction.

* * * * *